(12) United States Patent
Li et al.

(10) Patent No.: US 7,745,120 B2
(45) Date of Patent: Jun. 29, 2010

(54) CELL CULTURE AND METHOD FOR SCREENING FOR A COMPOUND USEFUL IN THE TREATMENT OR PREVENTION OF HEPATIC CIRRHOSIS

(75) Inventors: Wen-Tyng Li, Taipei (TW); Rung-Jiun Gau, Kaohsiung (TW); Yu-Shih Weng, Pingtung (TW); Cheng-Ta Hsieh, Tainan (TW); Pei-Shan Li, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 839 days.

(21) Appl. No.: 11/298,586

(22) Filed: Dec. 12, 2005

(65) Prior Publication Data

US 2006/0172416 A1 Aug. 3, 2006

(30) Foreign Application Priority Data

Dec. 28, 2004 (TW) .............................. 93141016 A

(51) Int. Cl.
*C12Q 1/68* (2006.01)
*C12Q 1/66* (2006.01)
*C12N 5/071* (2010.01)
*C12N 5/00* (2010.01)

(52) U.S. Cl. .............................. 435/6; 435/7.21; 435/8; 435/370; 435/373

(58) Field of Classification Search ...................... 435/6, 435/7.21, 8, 370, 373
See application file for complete search history.

(56) References Cited

FOREIGN PATENT DOCUMENTS

TW 200424215 11/2004
WO 02/48318 6/2002

OTHER PUBLICATIONS

Schaefer et al. (2003) 162:1771-1780.*
Davis et al. (1987) J. Biol. Chem. 262:10280-10286.*
Greenwel et al. (2000) Hepatol. 31:109-116.*
Tokiwa et al. (1999) in Vitro Cell. Dev. Biol.—Animal 35:246-247.*
Ueiki et al. (1998) Biochim. Biophys. Acta 1403:28-36.*
Prakinson et al., The effects of gender, age, ethnicity, and liver cirrhosis on cytochrome P450 enzyme activity in human liver microsomes and inducibility in cultured human hepatocytes Toxicology and Applied Pharmacology vol. 199, Issue 3, Sep. 15, 2004, pp. 193-209.*
Uyama et al., , Journal of Hepatology 36 (2002) 590-599.*
Svegliati-Baroni G,et al., Intracellular signaling pathways involved in acetaldehyde-induced collagen and fibronectin gene expression in human hepatic stellate cells. Hepatology. May 2001;33(5):1130-40.*
Armendariz-Borunda J, et al., Transcriptional mechanisms of type I collagen gene expression are differentially regulated by interleukin-1 beta, tumor necrosis factor alpha, and transforming growth factor beta in Ito cells.J Biol Chem. Jul 15, 1992;267(20):14316-21.*
Apolinar Maya-Mendoza, et al; Gene Positional Changes Relative to the Nuclear Substructure During Carbon Tetrachloride-Induced Hepatic Fibrosis in Rats; Journal of Cellular Biochemistry; 2004; p. 1084-p. 1098.

* cited by examiner

*Primary Examiner*—Maria Leavitt
(74) *Attorney, Agent, or Firm*—Bacon & Thomas, PLLC

(57) ABSTRACT

The present invention provides a cell-culturing model and a method for screening compounds which can be applied in treating or preventing hepatic cirrhosis. The cell culturing model comprises a population of hepatocytes and hepatic stellate cells (HSCs) derived from co-culturing, and at least one population of the cells comprises a nucleotide sequence fragment of a reporter gene and a cell specific regulatory sequence. The cell-culturing model of the present invention can be applied in high throughput screening for effective compounds of medication, and also in understanding the functional mechanism of the effective compounds.

20 Claims, 13 Drawing Sheets

(a)

(b)

(a)

(b)

(c)

SEQUENCE LISTING

```
<160> NUMBER OF SEQ ID NOS: 20

<210> SEQ ID NO 1
<211> LENGTH: 23
<212> TYPE: DNA
<213> ORGANISM: Homo sapiens

<400> SEQUENCE: 1
atttgggact taactctttc agt                                            23

<210> SEQ ID NO 2
<211> LENGTH: 23
<212> TYPE: DNA
<213> ORGANISM: Homo sapiens
```

<400> SEQUENCE: 2
agaaaagcta ggacaaacgg agg                                    23

<210> SEQ ID NO 3
<211> LENGTH: 414
<212> TYPE: DNA
<213> ORGANISM: Homo sapiens
<220> FEATURE:
<221> NAME/KEY: promoter
<222> LOCATION: (1)..(414)
<223> OTHER INFORMATION: promoter of albumin

<400> SEQUENCE: 3
gggatcctta actctttcag tatgtcttat ttctaagcaa agtatttagt ttggttagta    60
attactaaac actgagaact aaattgcaaa caccaagaac taaaatgttc aagtgggaaa   120
ttacagttaa ataccatggt aatgaataaa aggtacaaat cgtttaaact cttatgtaaa   180
atttgataag atgttttaca caactttaat acattgacaa ggtcttgtgg agaaaacagt   240
tccagatggt aaatatacac aagggattta gtcaaacaat ttttttggcaa gaatattatg   300 aattttgtaa tcggttggca gccaatgaaa tacaaagatg agtctagtta ataatctaca   360
attattggtt aaagaagtat attagtgcta atttccctcc gtttgtccaa gctt         414

<210> SEQ ID NO 4
<211> LENGTH: 25
<212> TYPE: DNA
<213> ORGANISM: Artificial
<220> FEATURE:
<223> OTHER INFORMATION: plasmid of green fluorescent protein

<400> SEQUENCE: 4
cccgggatcc accggtcgcc accat                                  25

<210> SEQ ID NO 5
<211> LENGTH: 27
<212> TYPE: DNA
<213> ORGANISM: Artificial
<220> FEATURE:
<223> OTHER INFORMATION: plasmid of green fluorescent protein

<400> SEQUENCE: 5
gatttcggcc tattggttaa aaaatga                                27

<210> SEQ ID NO 6
<211> LENGTH: 21
<212> TYPE: DNA
<213> ORGANISM: Artificial
<220> FEATURE:
<223> OTHER INFORMATION: pMSV-hyg

<400> SEQUENCE: 6
tttcgacctg catcccgcca c                                      21

<210> SEQ ID NO 7
<211> LENGTH: 21
<212> TYPE: DNA
<213> ORGANISM: Artificial
<220> FEATURE:
<223> OTHER INFORMATION: pMSV-hyg

<400> SEQUENCE: 7
atcagctctt gttcggtcgg c                                      21

```
<210> SEQ ID NO 8
<211> LENGTH: 34
<212> TYPE: DNA
<213> ORGANISM: Homo sapiens

<400> SEQUENCE: 8
ctgtcctcgt ccgtatttaa gcagttgatc caga                                 34

<210> SEQ ID NO 9
<211> LENGTH: 28
<212> TYPE: DNA
<213> ORGANISM: Homo sapiens

<400> SEQUENCE: 9
gccaggcact tcacccgagg cacttcac                                        28

<210> SEQ ID NO 10
<211> LENGTH: 737
<212> TYPE: DNA
<213> ORGANISM: Homo sapiens
<220> FEATURE:
<221> NAME/KEY: promoter
<222> LOCATION: (1)..(737)
<223> OTHER INFORMATION: promoter of alpha-1-antitrypsin

<400> SEQUENCE: 10
ggatcctcac ccgaggcact tcacaagcat gcttgggaat gaaacttcca actctttggg    60
atgcaggtga acagttcct ggttcagaga ggtgaagcgg cctgcctgag gcagcacagc    120
tcttctttac agatgtgctt ccccacctct accctgtctc acggcccccc atgccagcct   180
gacggttgtg tctgcctcag tcatgctcca ttttccatc gggaccatca agagggtgtt   240
tgtgtctaag gctgactggg taactttgga tgagcggtct ctccgctctg agcctgtttc   300
ctcatctgtc aaatgggctc taacccactc tgatctccca gggcggcagt aagtcttcag   360
catcaggcat tttggggtga ctcagtaaat ggtagatctt gctaccagtg aacagccac    420 taaggattct gcagtgagag cagagggcca gctaagtggt actctcccag agactgtctg   480
actcacgcca ccccctccac cttggacaca ggacgctgtg gtttctgagc caggtacaat   540
gactcctttc ggtaagtgca gtggaagctg tacactgccc aggcaaagcg tccgggcagc   600
gtaggcgggc gactcagatc ccagccagtg gacttagccc ctgtttgctc ctccgataac   660
tggggtgacc ttggttaata ttcaccagca gcctccccg ttgcccctct ggatcaactg    720
cttaaatacg gaagctt                                                    737

<210> SEQ ID NO 11
<211> LENGTH: 26
<212> TYPE: DNA
<213> ORGANISM: Homo sapiens

<400> SEQUENCE: 11
agatctccat tccaactccc aattgg                                          26

<210> SEQ ID NO 12
<211> LENGTH: 25
<212> TYPE: DNA
<213> ORGANISM: Homo sapiens

<400> SEQUENCE: 12
agatctagca gaagaattga catcc                                           25
```

<210> SEQ ID NO 13
<211> LENGTH: 27
<212> TYPE: DNA
<213> ORGANISM: Homo sapiens

<400> SEQUENCE: 13
aagcttcgat atagagtatg gttgcac                                            27

<210> SEQ ID NO 14
<211> LENGTH: 411
<212> TYPE: DNA
<213> ORGANISM: Homo sapiens
<220> FEATURE:
<221> NAME/KEY: promoter
<222> LOCATION: (1)..(411)
<223> OTHER INFORMATION: type I collagen alpha-I promoter

<400> SEQUENCE: 14

```
atctccattc caactcccaa attgggggcc gggccaggca gctctgattg gctggggcac          60
gggcggccgg ctcccctct ccgaggggca gggttcctcc ctgctctcca tcaggacagt         120
ataaaagggg cccgggccag tcgtcggagc agacgggagt ttctcctcgg ggtcggagca        180
ggaggcacgc ggagtgtgag gccacgcatg agcggacgct aaccccctcc ccagccacaa        240
agagtctaca tgtctagggt ctagacatgt tcagctttgt ggacctccgg ctcctgctcc        300
tcttagcggc caccgccctc ctgacgcacg gccaagagga aggccaagtc gagggccaag        360
acgaagacag taagtcccaa acttttggga gtgcaaggat actctatatc g                411
```

<210> SEQ ID NO 15
<211> LENGTH: 952
<212> TYPE: DNA
<213> ORGANISM: Homo sapiens
<220> FEATURE:
<221> NAME/KEY: promoter
<222> LOCATION: (1)..(952)
<223> OTHER INFORMATION: type I collagen alpha-I promoter

<400> SEQUENCE: 15

```
atctagcaga agaattgaca tcctcaaaat taaaactccc ttgcctgcac ccctccctca         60
gatatctgat tcttaatgtc tagaaaggaa tctgtaaatt gttccccaaa tattcctaag       120
ctccatcccc tagccacacc agaagacacc cccaaacagg cacatctttt taattcccag       180
cttcctctgt tttggagagg tcctcagcat gcctctttat gcccctccct tagctcttgc       240
caggatatca gagggtgact ggggcacagc caggaggacc cctcccccaa cacccccaac       300
ccttccacct ttggaagtct ccccacccag ctccccagtt ccccagttcc acttcttcta       360
gattggaggt cccaggaaga gagcagaggg gcaccctac ccactggtta gcccacgcca       420
ttctgaggac ccagctgcac ccctaccaca gcacctctgg cccaggctgg gctgggggc        480 tggggaggca gagctgcgaa gaggggagat gtggggtgga ctcccttccc tcctcctccc       540
cctctccatt ccaactccca aattgggggc cgggccaggc agctctgatt ggctggggca       600
cgggcggccg gctcccctc tccgagggc agggttcctc cctgctctcc atcaggacag        660
tataaagggg gcccgggcca gtcgtcggag cagacgggag tttctcctcg gggtcggagc       720
aggaggcacg cggagtgtga ggccacgcat gagcggacgc taaccccctc cccagccaca       780
aagagtctac atgtctaggg tctagacatg ttcagctttg tggacctccg gctcctgctc       840
ctcttagcgg ccaccgccct cctgacgcac ggccaagagg aaggccaagt cgagggccaa       900
gacgaagaca gtaagtccca aacttttggg agtgcaagga tactctatat cg              952
```

<210> SEQ ID NO 16
<211> LENGTH: 35
<212> TYPE: DNA
<213> ORGANISM: Homo sapiens

<400> SEQUENCE: 16
cgcggatccc attaccaccc tgagtcattt tgctc                              35

<210> SEQ ID NO 17
<211> LENGTH: 36
<212> TYPE: DNA
<213> ORGANISM: Homo sapiens

<400> SEQUENCE: 17
acgcaagctt gtctagcact tagacatgca gacttc                             36

<210> SEQ ID NO 18
<211> LENGTH: 2431
<212> TYPE: DNA
<213> ORGANISM: Homo sapiens
<220> FEATURE:
<221> NAME/KEY: promoter
<222> LOCATION: (1)..(2431)
<223> OTHER INFORMATION: type I collagen alpha-I promoter

<400> SEQUENCE: 18
cattaccacc ctgagtcatt tgctcagaa ttagtctctg actctcagca acacaggaca      60
aatacacaca tatgccctgc aaaggtaatt cagcacagtg gtaacaatga ttcttagaaa    120
tcatttctca ctcttctgat atgcagaaaa aaatttgtta tgatgtagta ttgaagtttt    180
tctttcctga taaaaatgat ttccacttta aaagtttttt gttagttctg taacggtgat    240
atttcaggga aatgttaaaa atgttcttgg aatatacaat tcaacctcag gtcttttgtt    300
gttgttgttc ctagaaccta gaaaacttca acattgttg cctagttaga aaaaaatttg     360
aatgtggatt gctccctgta aaccccttc taggaatgac cagtaaccct ttcaaattct     420
ttcactccca gttacttcaa aaaatcatcc aaagtggtct cccaagtgag tgcctttaat    480
tagaataaaa caagagttta ttatagtttt tggttatcca cttttacttg cattaacctt    540
tttttcttct tttacattta gaaagagtaa cctgctttag aatagtccct tttatttaca    600
gaagctgctg atggagttaa cttctgcaga aattcttcct taaggcaaag caaaaaaagc    660 ggggagggg tgggggaag gaagggaaaa agattctcag ggaactacag cccacttgct       720
tctgtttctt agagacagaa ctgacctaaa gatgccccct ttgcgatgac ttctgggata    780
gagcagcact ctaactaggc ccccgctgcc tcatggggac cttaggcaag tagaggagag    840
gcctgacaca cacacacaca cacacacaca cacacgca cacgcgcg cgcgcgcaca        900 cacacacaca cagcctttca aacctagggc ctggaatgcc atcccaagag gctttagaaa    960
aaggcacagg acctttggcc tcccacctca gggtcaaagt accagttcct cctctcccta   1020
gtagggagtg gagggttgga tggaggcggc cagagaagag ggaagttggg tgctggggag   1080
agagttaaca tccacgttgg tgggcgcact gcttggggtg ttaccagcga agattacgaa   1140
gaccccaagc tcgaatcaga agggcctctg gatgtgctag ggaggtgct tgggtgtaac    1200 tgtaagagat gggacagaga gtaagcagca aggtcaagag gaccggggg gctcacggga    1260 gggttgaagg gtccaggctc agggtagaac tggtaaatcc agacaaggag cccatggaga   1320
aggggagggg agactggaaa ccatgaaaga tcccccaccg cagcctcaga aaggagagac   1380
tgagaaataa gttctcggtc tccaggtcgg ttggagtcgt gtcggagtgc cagaccatcc   1440

-continued

```
cccaaaagac cctctttgga atgagcctca gcaaaggcaa gctaggaggt cgaaggactt   1500
ccccaggtga ctcggtctag tctagagttc gcaaagccta tcctccctgt agccgggtgc   1560
caagcagcct cgagcctgct ccccagccca cctgccaaca aaaggcgccc tccgactgca   1620
acccagccct ccacagacag gacccgccct ttcccgaagt cataagacaa agagagtgca   1680
tcactgctga aacagtgggc gcacacgagc cccaaagcta gagaaaagct ggaaggggct   1740
gggggcgggg tgcaggggtg gaggggcggg gaggcgggct ccggctgcgc cacgctatcg   1800
agtcttccct ccctccttct ctgccccctc cgctcccgct ggagccctcc accctacaag   1860
tggcctacag ggcacaggtg aggcgggact ggacagctcc tgctttgatc gccggagatc   1920
tgcaaattct gcccatgtcg gggctgcaga gcactccgac gtgtcccata gtgtttccaa   1980
acttggaaag ggcggggag ggcgggagga tgcggagggc ggaggtatgc agacaacgag   2040
tcagagtttc cccttgaaag cctcaaaagt gtccacgtcc tcaaaaagaa tggaaccaat   2100
ttaagaagcc agccccgtgg ccacgtccct tcccccattc gctcctcct ctgcgccccc    2160 gcaggctcct cccagctgtg gctgcccggg ccccagccc cagccctccc attggtggag    2220 gccctttttgg aggcaccta gggccaggga aactttttgcc gtataaatag ggcagatccg   2280
ggctttatta ttttagcacc acggcagcag gaggtttcgg ctaagttgga ggtactggcc   2340
acgactgcat gcccgcgccc gccaggtgat acctccgccg gtgacccagg ggctctgcga   2400
cacaaggagt ctgcatgtct aagtgctaga c                                  2431
```

<210> SEQ ID NO 19
<211> LENGTH: 26
<212> TYPE: DNA
<213> ORGANISM: Artificial
<220> FEATURE:
<223> OTHER INFORMATION: pDsRed2-1

<400> SEQUENCE: 19
aagcttccat ggcctcctcc gagaac                                          26

<210> SEQ ID NO 20
<211> LENGTH: 24
<212> TYPE: DNA
<213> ORGANISM: Artificial
<220> FEATURE:
<223> OTHER INFORMATION: pDsRed2-1

<400> SEQUENCE: 20
acctcgagaa atgtggtatg gctg                                            24

CELL CULTURE AND METHOD FOR SCREENING FOR A COMPOUND USEFUL IN THE TREATMENT OR PREVENTION OF HEPATIC CIRRHOSIS

BACKGROUND OF THE INVENTION

1. Field of the Invention

The present invention relates to a cell culturing model and a method for drug screening, more particularly, to a cell culturing model and a method using modified liver cells and hepatic stellate cells in high throughput drug screening for hepatic cirrhosis treatment.

2. Description of Related Art

Hepatic cirrhosis is often resulted from the damage to hepatocytes by alcohol and drugs, or virus infection. Damaged hepatocytes release certain signals to activate hepatic stellate cells (HSCs) in liver tissue into myofibroblasts (MFs). MFs are capable of secreting large varieties of extracellular matrix (ECM), including collagen, fibronectin, laminin and proteoglycan. The accumulation of excess extracellular matrix causes liver fibrosis. In the meantime, accumulated extracellular matrix further obstructs hepatocytes from the supply of oxygen and nutrients, and therefore leads to necrosis. To sum up, hepatic cirrhosis is the result of necrosis of hepatocytes and excessive secretion of extracellular matrix by HSCs, due to the imbalance between the rates of degradation and bio-synthesis of extracellular matrix.

Screening methods for anti-hepatic cirrhosis drugs include in vitro screening by cell culture and in vivo screening by animal models. In vitro screening method by cell culture often uses single type of cells, such as HepG2 cell-line, primary rat hepatocytes, or Chang liver cells derived from human liver. Liver-protecting drugs are treated on the alcohol, carbon tetrachloride ($CCl_4$) or α-galactosamine (GaIn) damaged cells, and albumin production, MTT analysis, and the activities of glutathione-S-transferase (GST) or cytochrome P450 are measured, which serve as indication of the recovery of damaged cells. Besides, HSCs or MFs can also be used to observe how the drug inhibits their activities. The expression of α-actin and desmin, collagen production, and the activities of MMP-3 (matrix metalloproteease-3) or -9 usually serve as indicators.

Mice, rats, rabbits and canines are commonly used as animal models for liver protecting drug screening. Acute or chronic hepatic cirrhosis can be induced by the treatment of $CCl_4$ or GaIn, bile duct ligation or *Schistosoma japonicum* infection. Recovery of liver damaged animals are observed after administering liver-protecting drugs.

However, using animal experiments to demonstrate the efficacy of newly synthesized drugs conflicts he aspects of economy and humanity. Current in vitro cell model uses single type of cells only, either hepatocytes or HSCs, which is not in accordance with the physiological condition of hepatic cirrhosis. Deviation is likely to occur. A selected drug with therapeutic efficacy should be able to enhance the function of hepatocytes, and also inhibit the activation of HSCs and the production of extracelluar matrix. Therefore, it is necessary to develop an appropriate cell model in accordance with the physiological condition of cirrhotic livers.

Present high throughput screening apparatus for new drugs uses single type of monolayer cells. Monolayer-cells cannot display the real physical condition, not to mention performing screening on several types of cells at the same time. As a result, the actual function and the tissue specificity of the drug cannot be accurately detected, and therefore cause the omission of other important uses which will lead to the misconception of effectiveness. This is also the reason for criticism of the high-speed screening technique for new drugs.

The invention is to develop a cell-culturing model for high throughput screening anti-hepatic cirrhosis drugs. The fluorescence released from reporter genes in genetic modified hepatocytes and HSCs can be detected by a fluorescence reader, which provide a quick and sensitive platform for real-time examination of cell condition and therefore increase the accuracy of drug screening. Experiments on animals may also be replaced in the future to significantly decrease the costs and time for developing a new drug screening.

SUMMARY OF THE INVENTION

To develop a system that is mimic hepatic cirrhosis cell model, provide stable cell sources, and perform reaction and detection at the same time, the present invention uses genetically modified hepatic stellate cells (HSCs) or/and hepatocytes containing cell specific regulatory sequence fused with reporter genes to create a dynamic detecting system for live cell activities. Along with the design of cell chips, a research platform on liver tissue can be established. Meanwhile, multi-layer co-culturing HSCs with hepatocytes will agree with the structure of the liver tissue even better, which will reflect the actual cellular interaction under drug treatment.

The present invention encloses a cell model for anti-liver cirrhotic drug screening, wherein genetically modified hepatocytes and HSCs are used as the reaction tools. The efficiency of test drugs can be through the fluorescence signals expressed by reporter genes. Thus the present invention allows a fast, sensitive and real-time examination of multiple cellular condition. Furthermore, the mechanism of drugs can be further elucidated.

The present invention also provides a cell model for anti-liver cirrhotic drug screening, in which the live cell activity can be detected and monitored in long-term.

The present invention provides a cell model for anti-liver cirrhotic drug screening, which comprises a population of cells, wherein the population of cells are derived from co-cultured hepatocytes and HSCs, wherein at least one cell type in the population of cells containing a cell specific regulatory sequence and a nucleotide sequence of a reporter gene.

The population of cells in the cell model of the present invention are co-cultured in a culture medium and a culture material coated with an extracellular matrix. The ratio of initial seeding density of HSCs and hepatocytes is not specified, preferably is 1:10.

The co-culture method of HSCs and hepatocytes in the cell model of the present invention can be referred to a publication by Naoki Uyama et al (J. Hepatology. 36:590-599, 2002), which can be mixed co-culture or separated co-culture.

The term "regulatory sequence" is a promoter, an enhancer or any DNA fragments to which a regulatory protein (for example, transcription factors) priory binds.

The cell specific regulatory sequences in the present invention are hepatocyte- or HSC-specific promoters. The term "cell specific promoters" means a nucleotide fragment positioned upstream of the gene, which binds RNA polymerase to form a transcription initiation complex, and transcription proceeds. The promoters turn on different gene expression in different cells y, for example, albumin promoter (ALB) and α-I antitrypsin promoter are hepatocyte specific promoters. Collagen type I promoter is one of the HSCs specific promoter.

The products of the reporter genes preferably used in the cell model of the present invention can be detected and quantitatively measured, such as β-galactosidase, chloramphenicol acetyl transferase (CAT), luciferase, or fluorescence proteins. The reporter genes further comprise positive selection markers, for example, antibiotic resistance genes such as hygromycin resistant gene or neomycin resistant gene.

The HSCs and hepatocytes in the cell culturing model of the present invention can further be immortalized. A nucleotide sequence of an immortalization gene can be carried in these cells.

The immortalization gene used in the present invention is not limited, preferably is Human telomerase reverse transcriptase catalytic subunit (hTERT) gene or large T-antigen (Tag) of Simian virus 40 (SV40) genes.

In the cell model of the present invention, the fragments of cell specific regulatory sequences, the reporter genes, and the immortalization genes can be conducted into cells by transfection. The suitable methods of transfection are electroporation, lipofection, calcium phosphate, DEAE-dextran, etc.

The extracellular matrix in the cell model of the present invention can be any extracellular matrix used in the skilled art, preferably is collagen or Matrigel.

A method for screening drugs for hepatic cirrhosis treatment with a cell model is further disclosed, which comprises steps of: (a) applying a testing compound in said cell model, wherein said cell model is a cell population derived from hepatocytes and HSCs, and one of the cell population having a cell specific regulatory sequence and a nucleotide sequence of a reporter gene; (b) estimating cell activity of said cell population or the expression of a reporter gene; (c) comparing said cell activity of the cell population or the expression of said reporter gene; and (d) analyzing the correlation of said testing compound for hepatic cirrhosis inhibition.

According to the present invention, the testing compounds have the efficacy of anti-hepatic cirrhosis when the expression level of the reporter genes in HSCs is decreased and/or that in hepatocytes is increased, or when the activity of the HSCs is decreased and/or that of hepatocytes is increased.

Preferably, a step (a') is further included before or after said step (a) in the method of the present invention, in which a known material related to hepatic cirrhosis can be further applied in the cell model.

The methods to determine the expression level of the reporter gene in the present invention has no limitation, preferably to use a fluorescence reader, an ELISA Reader or a flow cytometer (FCM). The methods to measure cell activity in the present invention has no limitation, preferably by fluorescence intensity observation, RT-PCR, MTT assay or methylene blue assay.

Other objects, advantages, and novel features of the invention will become more apparent from the following detailed description when taken in conjunction with the accompanying drawings.

BRIEF DESCRIPTION OF THE DRAWINGS

FIG. 8(a) is the fluorescence result expressed from cells transfected with plasmid pLPLhyg-$P_{ALB5/3}$-EGFP; and FIG. 8(b) is with pLPLhyg-$P_{AAT}$-EGFP.

FIG. 9(a) is the fluorescence result expressed from cells transfected with plasmid pLPLhyg-$P_{ALB5/3}$-EGFP; and FIG. 9(b) is with pLPLhyg-$P_{AAT}$-EGFP.

FIG. 10(a) is the expression of HSCs transfected with pLP-Hyg-A3B1-DsRed; FIG. 10(b) is with pLP-Hyg-A5B1-DsRed; and FIG. 10(c) is with pLP-Hyg-COL1A2-DsRed.

DETAILED DESCRIPTION OF THE PREFERRED EMBODIMENT

Example 1

Figure 1A:
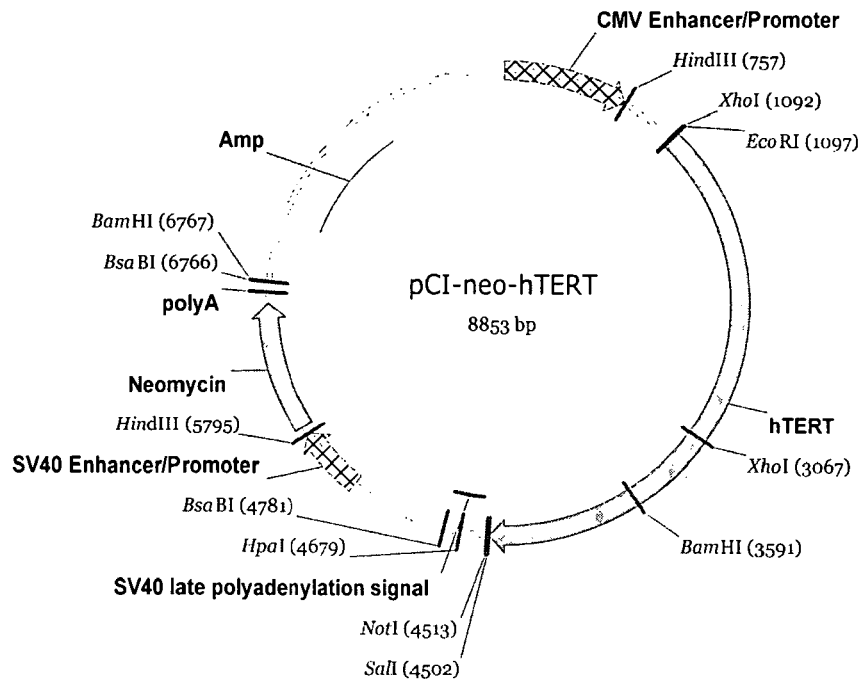
FIG. 1A is a restriction map of plasmid pC1-neo hTERT in example 1.
Figure 1B:
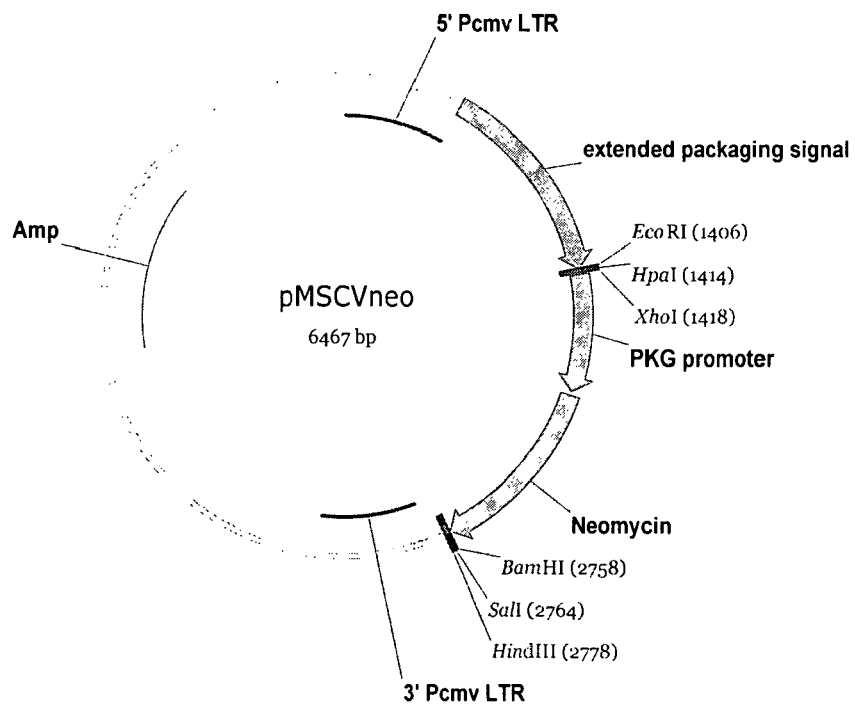
FIG. 1B is a restriction map of vector pMSCV-neo in example 1.
Figure 1C:
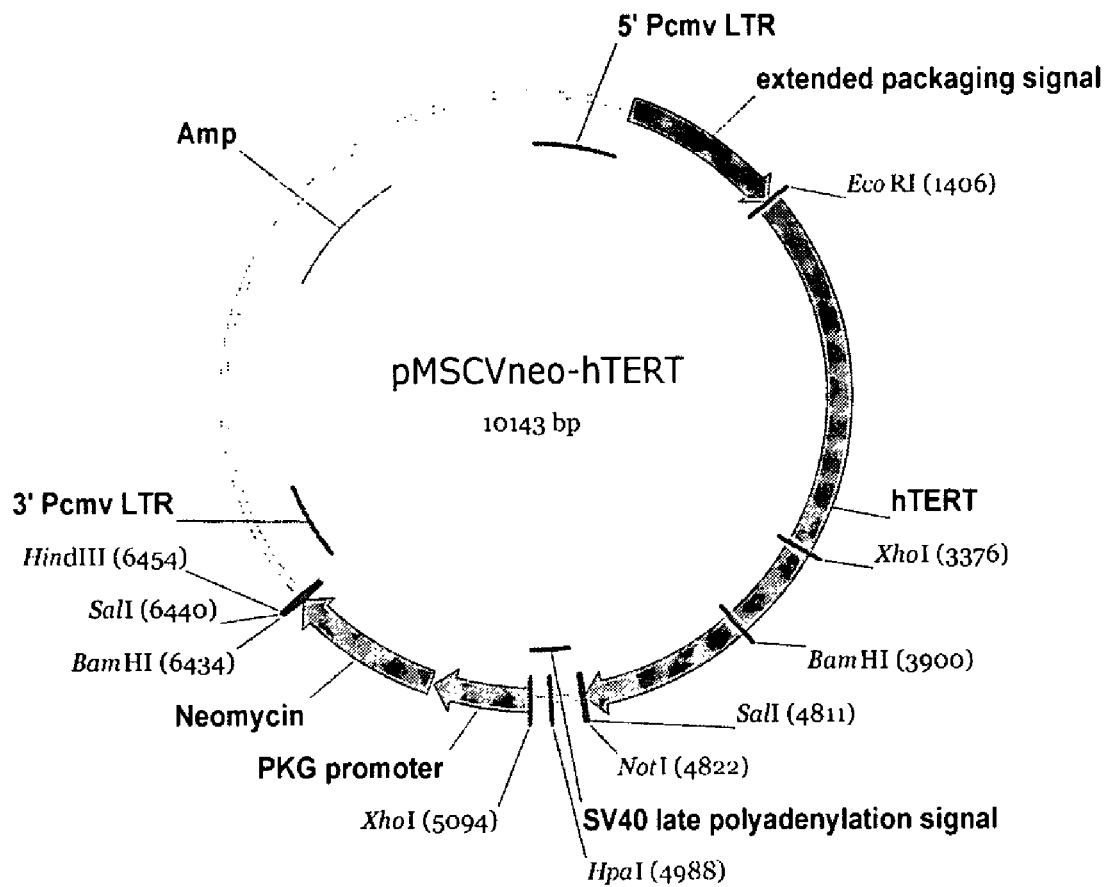
FIG. 1C is a restriction map of retroviral vector of pMSCV-neo hTERT in example 1.

Preparation of Retrovirus Particles Containing Immortalizing Plasmid and Transfection of the Cell Line In the present example, one of the cell lines used in the cell model was human HSC, which was transfected with virus particles carrying immortalizing vector. The plasmid pC1-neo hTERT (FIG. 1A, Promega Corporation) was restriction digested with EcoR I and Sat I, and pMSCV-neo (FIG. 1B, Clontech Laboratories, Inc.) plasmid was also digested with EcoR I and Xho I. The digested fragments were separated by electrophoresis, and desired fragments were purified with QIA quick Gel Extraction Kit (QIAGEN). Purified fragments were ligated via T4 DNA ligase, and the retroviral vector of pMSCV-neo hTERT was thus obtained (FIG. 1C).

The retroviral vector of pMSCV-neo hTERT constructed above was transfected into packing cells—RetroPack™pT67 or AmphoPack™-293 by Lipofectamine Reagents (Invitrogen Corporation). Culture medium containing retrovirus particles were collected and used to infect HSCs. An antibiotics—neomycin was added to restrain the growth of untransfected HSCs.

Figure 2A:
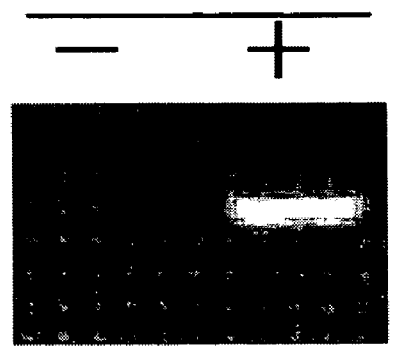
FIG. 2A is the result of an electrophoresis where the mRNA expression of neomycin gene in example 1 is confirmed.
Figure 2B:
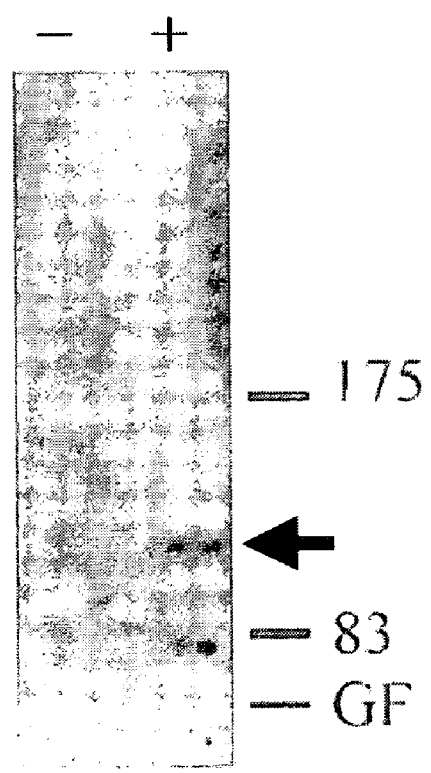
FIG. 2B is a result of Western blot in example 1 wherein the protein of hTERT is expressed.

The expression of neomycin from transfected HSCs was confirmed by RT-PCR. Please refer to FIG. 2A wherein the symbol "−" represents untransfected HSCs which expressed no mRNA product of neomycin gene was seen in electrophoresis. The symbol "+" represents neo-hTERT transfected HSCs. Furthermore, the presence of hTERT was confirmed by Western blot. As shown in FIG. 2B, the symbol "−" represents untransfected HSCs, and the symbol "+" represents neo-hTERT transfected HSCs. The arrow mark highlighted shows that hTERT protein was expressed from HSCs after transfection. The immortalized cell lines were stored in liquid nitrogen for further drug screening assays.

Example 2

Construction of Retroviral Vector Containing Albumin Promoter

In the present example, hepatocyte cell line used in the cell model was Huh-7 cells transfected with retroviral vector containing albumin promoter. The transfected cells in the present invention were selected by hygromycin. Besides the hygromycin resistant gene, the retroviral vector also contained a liver cell specific albumin promoter and an enhanced green fluorescence protein (EGFP) reporter gene.

To clone albumin promoter, the sequence of accession number 00178343 in GenBank was used to design primers hSA-3(SEQ ID NO.1) and hSA-5(SEQ ID NO.2). RT-PCR was performed with primers hSA-3 and hSA-5 to amplify albumin promoter fragment from human cDNA, the sequence of the amplified fragment is shown in SEQ ID NO.3.

The gene fragment of the enhanced green fluorescence protein (EGFP) was amplified with two primers of EGFP-1 (SEQ ID NO. 4) and EGFP-3 (SEQ ID NO. 5) from plasmid pEGFP-1 (FIG. 3A, Clontech Laboratories, Inc.) by PCR. Hygromicin resistant gene was cloned with two primers—hyg-1 (SEQ ID NO.6) and hyg-2 (SEQ ID NO. 7) from plasmid pMSCV-hyg (FIG. 3B, Clontech Laboratories, Inc.) by PCR.

Figure 4A:
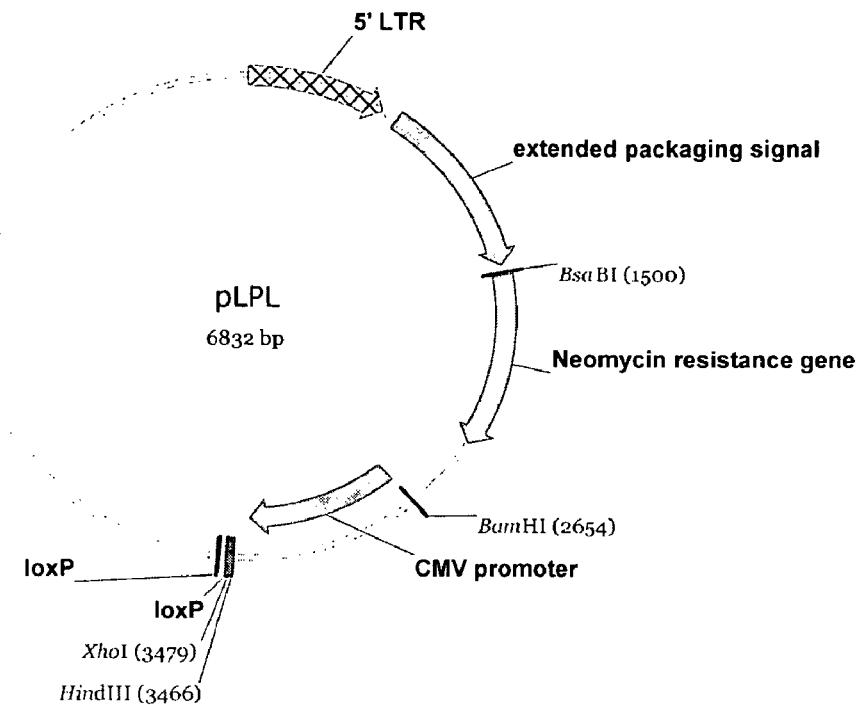
FIG. 4A is a restriction map of retroviral vector pLP-LNCX-2loxP in example 2.
Figure 4B:
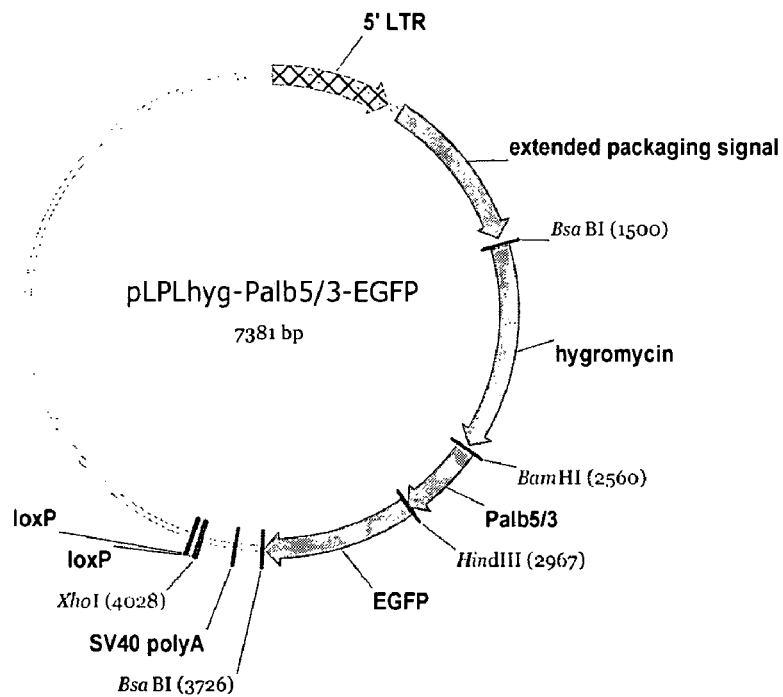
FIG. 4B is a restriction map of retroviral vector pLPLhyg-$P_{ALB5/3}$-EGFP in example 2.

The procedure of constructing retroviral vector encoding albumin promoter is described below. First, the hygromicin resistant gene was ligated to a retroviral vector—pLP-LNCX-2loxP (FIG. 4A) via T4 DNA ligase, then the EGFP gene fragment was also ligated to the same retroviral vector carring hygromicin resistant gene. Finally, albumin promoter was then ligated to the vector to obtain retroviral vector—pLPL-hyg-$P_{ALB5/3}$-EGFP (FIG. 4B).

Example 3

Construction of Retroviral Vector Carrying α-I-antitrypsin Promoter

In the present example, the cells used for the cell model can be Huh-7 cells transfected by a retrovirus particles carrying α-I-antitrypsin promoter. Besides liver cell specific promoter—α-I-antitrypsin promoter, the retroviral vector also encodes hygromicin resistant gene and EGFP gene.

The sequence of accession number 00177830 in GenBank containing liver specific α-I-antitrypsin promoter, which was used to design primers AAT-1 (SEQ ID NO.8) and AAT-2 (SEQ ID NO.9). RT-PCR was performed with primers AAT-1 and AAT-2 to amplify α-I-antitrypsin promoter fragment from human cDNA, and the sequence of the amplified fragment is shown in SEQ ID NO.10.

Figure 3A:
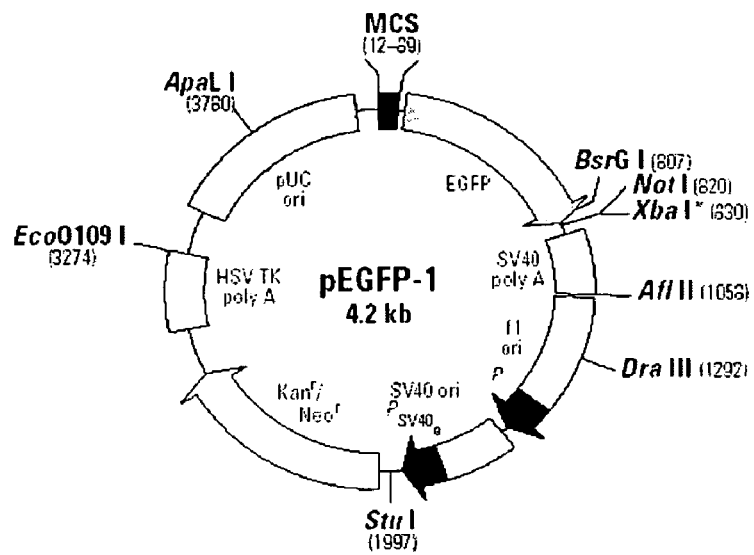
FIG. 3A is a restriction map of plasmid pEGFP-1 in example 2.
Figure 3B:
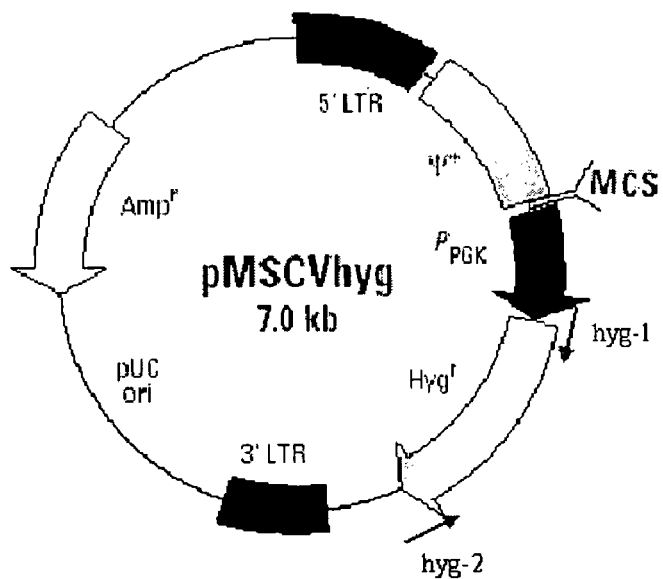
FIG. 3B is a restriction map of plasmid pMSCV-hyg in example 2.

As described in example 1, the EGFP gene was amplified with two primers—EGFP-1 (SEQ ID NO: 4) and EGFP-3 (SEQ ID NO: 5) from plasmid pEGFP-1 (FIG. 3A, Clontech Laboratories, Inc.). The hygromicin resistant gene was amplified from plasmid pMSCV-hyg (FIG. 3B, Clontech Laboratories, Inc.) by PCR.

Figure 5:
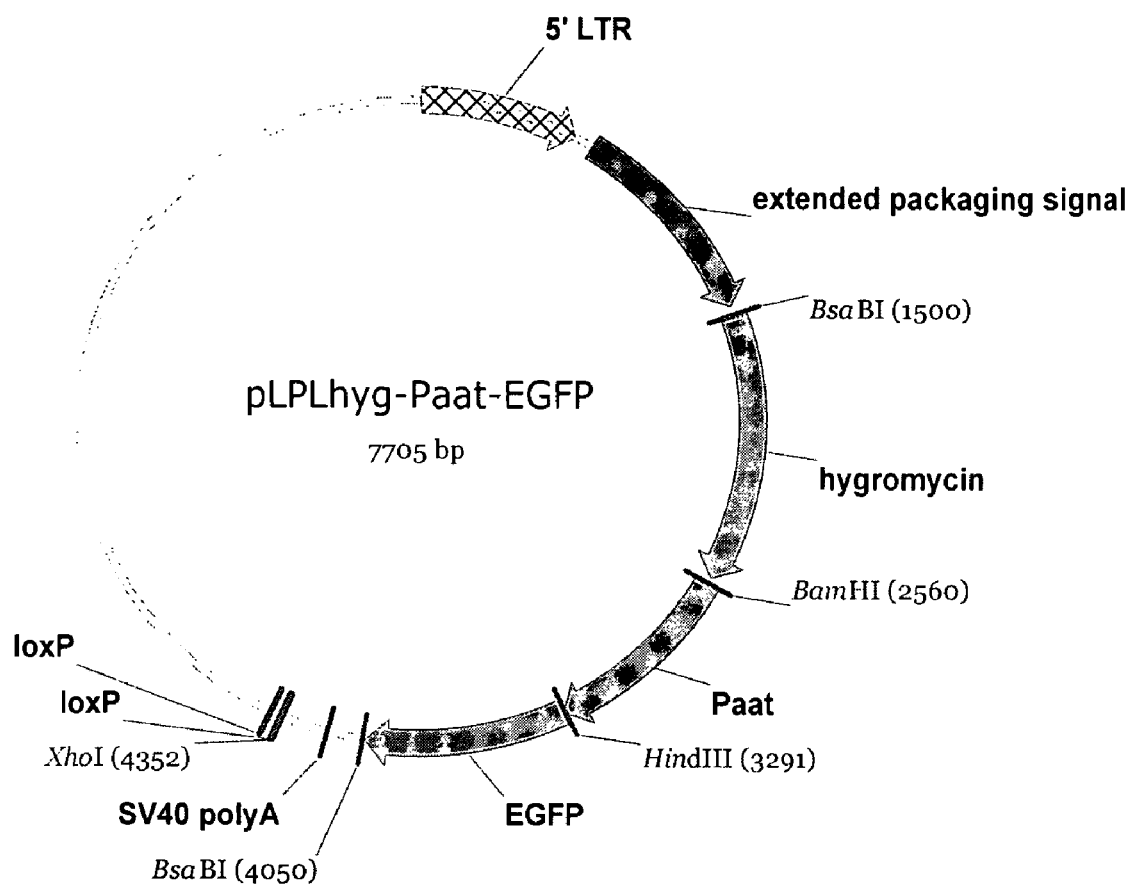
FIG. 5 is a restriction map of retroviral vector pLPLhyg-$P_{AAT}$-EGFP in example 3.

The construction procedures of the retroviral vector are similar to example 1. T4 DNA ligase is used to ligate hygromicin resistant gene, EGFP gene and α-I-antitrypsin promoter to the retroviral vector pLP-LNCX-2loxP (FIG. 4A), and a new retroviral vector—pLPLhyg-$P_{AAT}$-EGFP (FIG. 5) was obtained.

Example 4

Construction of Retroviral Vector Carrying Collagen Type I Promoter

Another cell used in the cell model was HSCs transfected by retroviral vector carrying collagen type I promoter. Type I collagen comprises COL1A1 and COL1 A2 promoters. The promoters in the present example were cloned and selected by hygromicin resistantance. The present retroviral vector contains not only hygromicin resistant gene but also HSC specific collagen type I promoter, and DsRed reporter gene.

To clone collagen COL1A1 promoter, the sequence of accession NO: 4755084 in GenBank was used for designing three oligonucleotide primers—COL-A3 (SEQ ID NO. 11), COL-A5 (SEQ ID NO. 12) and COL-B1 (SEQ ID NO. 13). Two fragments containing collagen type I promoter were amplified by RT-PCR from human HSC cDNA, as shown in SEQ ID NO. 14—A3B1 and SEQ ID NO. 15—A5B1.

To clone collagen COL1A2 promoter, the sequence of accession NO: 2735714 in GenBank was used for designing two oligonucleotide primers—COL-A2-1 (SEQ ID NO. 16) and COL-A2-2 (SEQ ID NO. 17). One gene fragment containing COL-α I promoter was amplified from human HSC cDNA, and the sequence is shown in SEQ ID NO.18.

Figure 6:
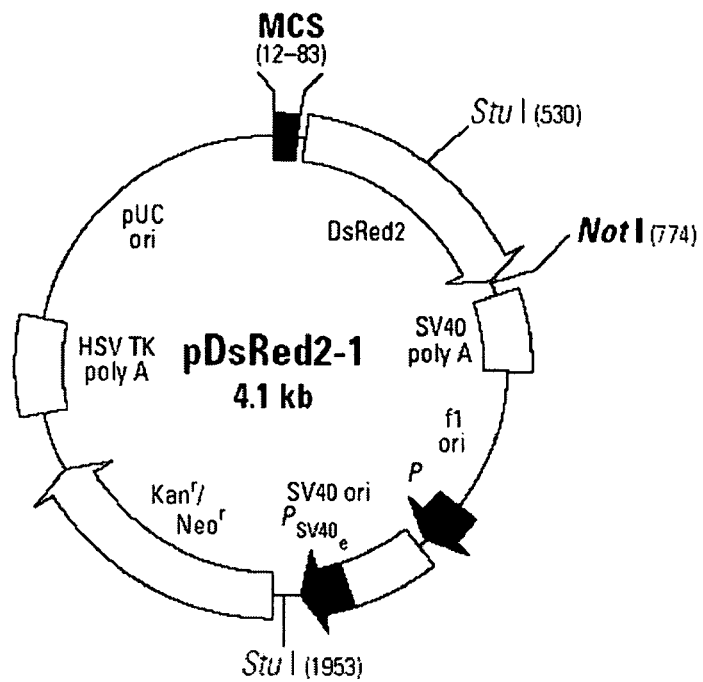
FIG. 6 is a restriction map of plasmid pDsRed2-1 in example 4.

DsRed reporter gene was amplified with two primers—DS-1 (SEQ ID NO: 19) and DS-2 (SEQ ID NO: 20) from plasmid pDsRed2-1 (FIG. 6, Clontech Laboratories, Inc.) by PCR. Hygromicin resistant gene was amplified with two primers—hyg-1 (SEQ ID NO: 6) and hyg-2 (SEQ ID NO: 7) from plasmid pMSCV-hyg (FIG. 3B, Clontech Laboratories, Inc. ) by PCR.

Figure 7A:
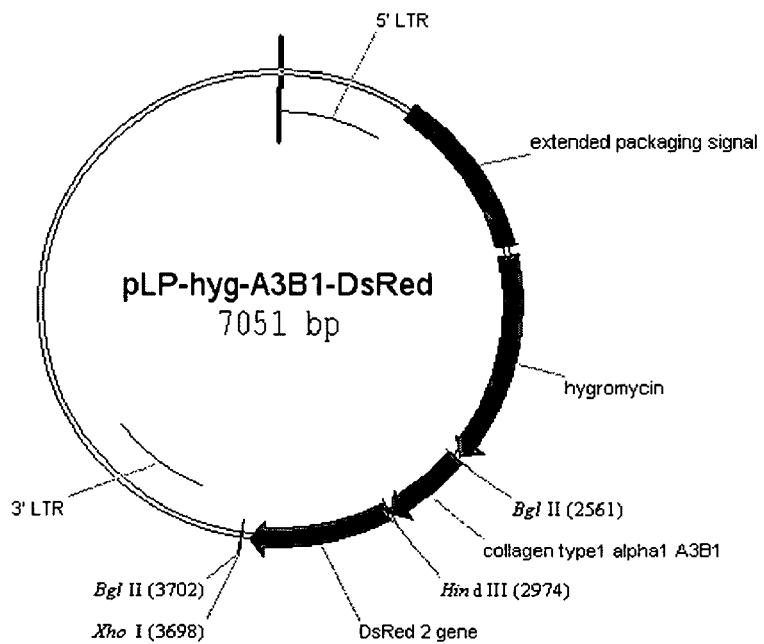
FIG. 7A is a restriction map of retroviral vector pLP-Hyg-A3B1-DsRed in example 4.
Figure 7B:
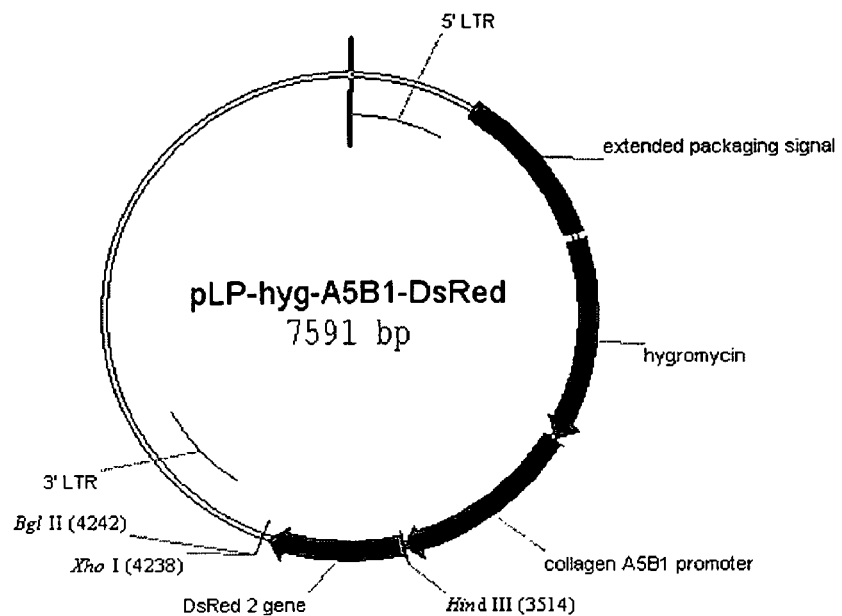
FIG. 7B is a restriction map of retroviral vector pLP-Hyg-A5B1-DsRed in example 4.
Figure 7C:
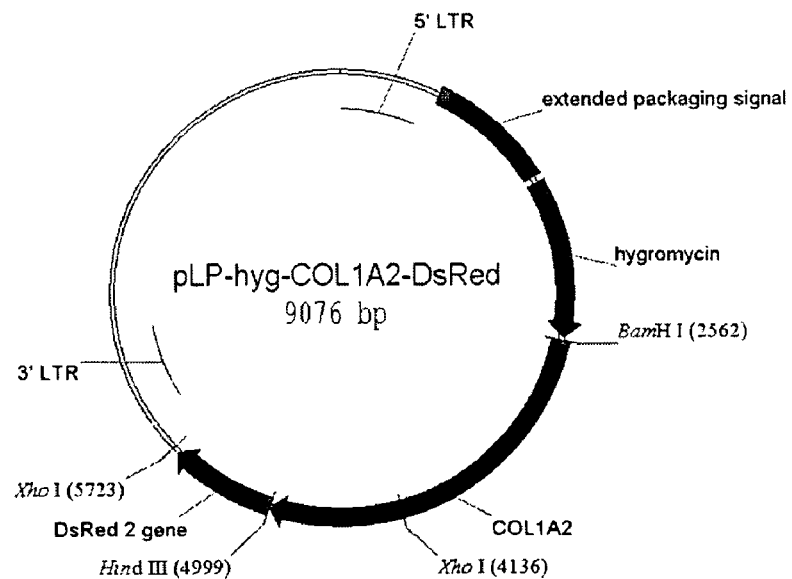
FIG. 7C is a restriction map of retroviral vector pLP-Hyg-COL1A2-DsRed in example 4.

The construction procedure of the retroviral vector was similar to example 1. T4 DNA ligase was used to ligate hygromicin resistant gene, DsRed gene and promoter genes (A3B1, A5B1 and COL1A2, respectively cloned) to the retroviral vector pLP-LNCX-2loxP (FIG. 4A). Three kinds of retroviral vector are obtained: pLP-Hyg-A3B1-DsRed (FIG. 7A), pLP-Hyg-A5B1-DsRed (FIG. 7B) and pLP-Hyg-COL1A2-DsRed (FIG. 7C).

Example 5

Transfection of Cells with Virus Particles Carrying Retroviral Vector

Retroviral vectors carrying different hepatocyte specific promoters constructed from examples 2 and 3 were transformed into the packaging cells to obtain virus particles.

Similarly, retroviral vectors carrying different HSC specific promoters constructed from examples 4 were also transformed into another packaging cells to obtain virus particles. These viral particles were used to infect liver cells, respectively.

Retroviral vectors—pLpLhyg-P$_{Alb5/3}$-EGFP (FIG. 4B), pLpLhyg-P$_{AAT}$-EGFP (FIG. 5), pLpHyg-A3B1-DsRed (FIG. 7A), pLpHyg-A5B1-DsRed (FIG. 7B) and pLpHyg-COL1A2-DsRed (FIG. 7C) were delivered into packaging cell lines—RetroPack™ pT67 or AmphoPack™-293 (AP293) by liposome-mediated transfection (Invitrogen Corporation). Failed transfected cells were killed by antibiotic-hygromicin or neomycin. The supernatant of the culture medium of transfected pT67 or AP293 cells were collected and then subjected to RT-PCR for a further confirmation of successfully production of viral particles.

The culture medium containing retroviral particles were collected and then added into targeted cell culture. Hygromicin was applied to kill the cells with failed infection. PCR was conducted to confirm that the DNA carried by virus was inserted into the chromosomes of the infected cells, and RT-PCR was further used to detect the expression of the fluorescence genes.

Example 6

Examining Genetically Modified Cell Lines

The fluorescence signal expressed from transfected cells of example 5 was observed under a fluorescence microscope, and the fluorescence intensity was analyzed by image analysis software. Fluorescence intensity of EGFP was determined by a fluorescence reader and an fluorescence ELISA reader. The excitation wavelength was 488 nm, and the emission wavelength was 510 nm while the green fluorescence from the EGFP gene was detected. When the red fluorescence from DsRed gene was detected, the excitation wavelength was 558 nm, and the emission wavelength was 583 nm. A flow cytometry (for example, FACSCalibur, Becton Dickinson, Inc.) can also be used to determine the intensity of fluorescence.

Figure 8:
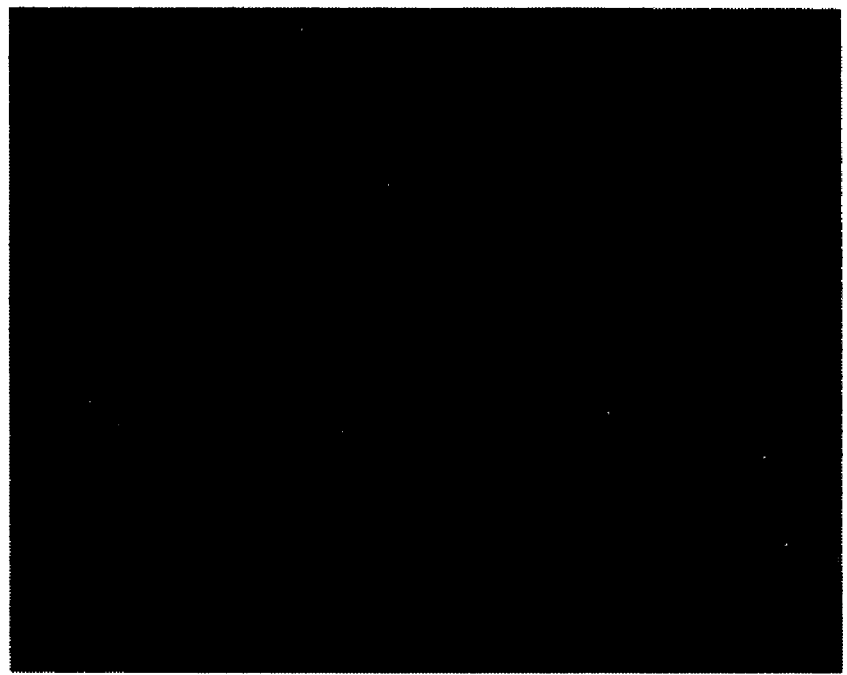
FIG. 8 reveals the green fluorescence expressed by Huh-7cell line transfected with two plasmids respectively in example 5.
Figure 8:
Figure 9:
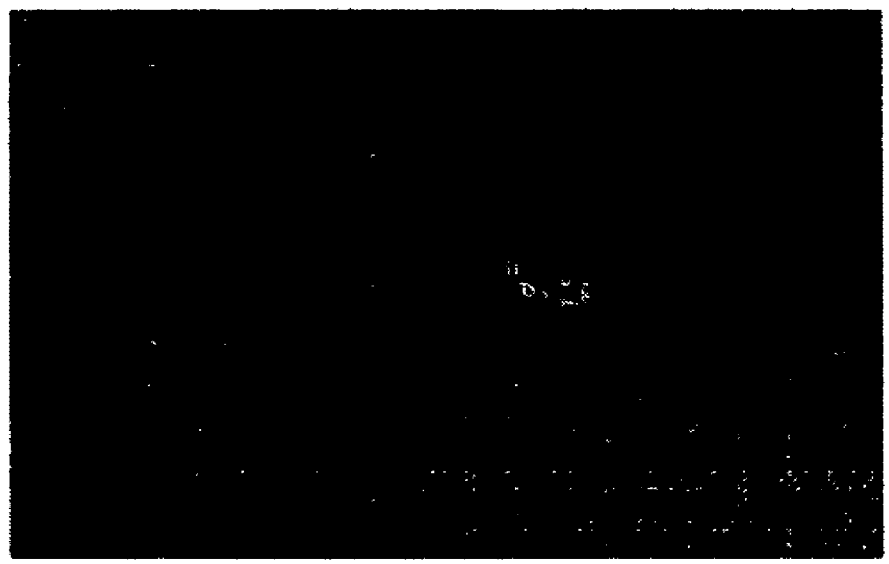
FIG. 9 reveals the green fluorescence expressed by HepG2/C3A cell line transfected with two plasmids respectively in example 5.
Figure 9:
Figure 10:
FIG. 10 reveals the red fluorescence expressed by HSCs transfected with 3 plasmids respectively in example 6.
Figure 10:
Figure 10:

The results are shown in FIG. 8 and FIG. 9. FIG. 8(a) shows the green fluorescence expressed from Huh-7 cells carrying pLPLhyg-P$_{ALB5/3}$-EGFP, and FIG. 8(b) shows the green fluorescence from Huh-7 cells carrying pLPLhyg-P$_{AAT}$-EGFP. Furthermore, green fluorescence was also expressed from the cell line-HepG2/C3A transfected with pLPLhyg-P$_{ALB5/3}$-EGFP and pLPLhyg-P$_{AAT}$-EGFP. As shown in FIG. (9), FIG. 9(a) represents cells with pLPLhyg-P$_{ALB5/3}$-EGFP, and FIG. 9(b) represents cells with pLPLhyg-P$_{AAT}$-EGFP. Moreover, three transfected HSCs expressed red fluorescence, as shown in FIGS. 10(a), (b) and (c).

Example 7

Establishment of Cell Model for Drug Screening

Modified human HSCs and Huh-7 cells obtained from examples 1 and 6 were co-cultured via layer by layer culturing. Immortalized human HSCs were cultured in a 24-well culture plate, wherein each well was coated with extracellular matrix before use. The extracellular maxtrix used in the present example was Type I collagen or Matrigel. Six hours after the HSCs were attached, Huh-7 cells carrying albumin promoter (pLpLhyg-P$_{Alb5/3}$-EGFP) (Huh-7$_{PALB-EGFP}$) were subsequently cultured on the top of the attached HSCs.

Figure 11A:
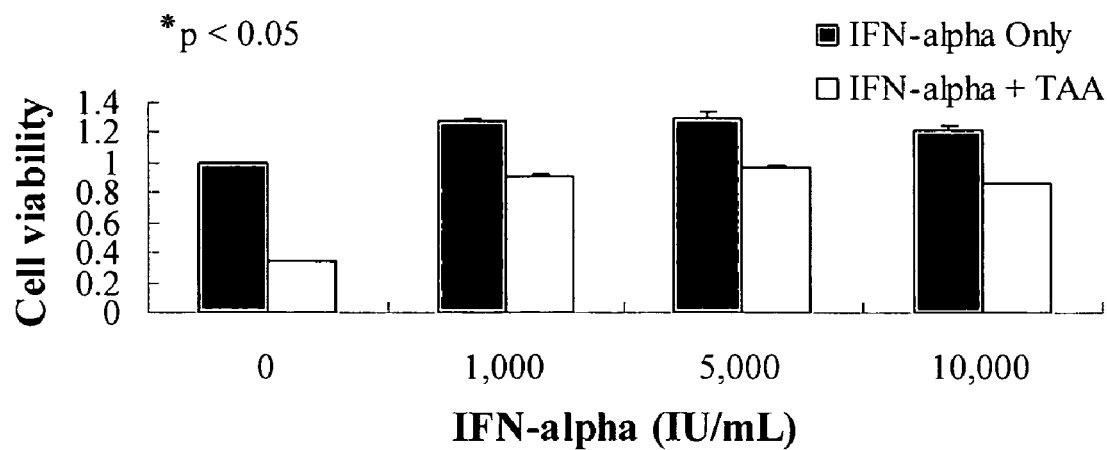
FIG. 11A is the result of methylene blue assay to evaluate the effect of interferon-α. The result shows that interferon-α decreased the damage from thioacetamide in Huh-7$_{PALB-EGFP}$ and immortalized HSC coculture
Figure 11B:
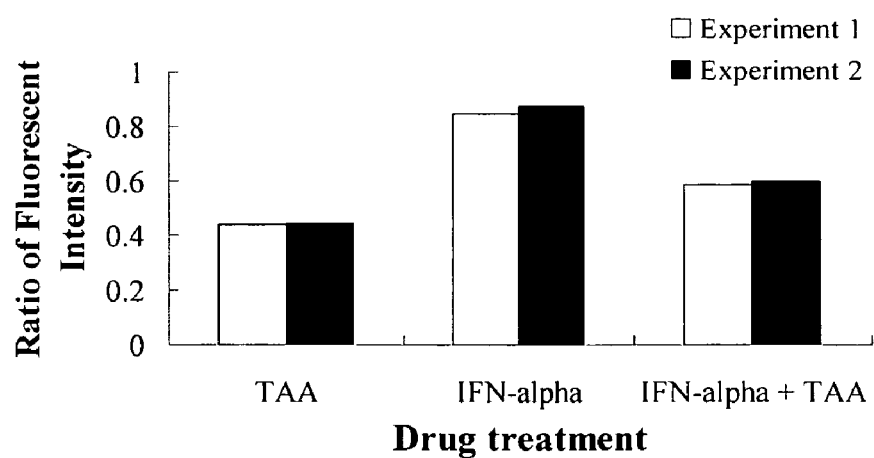
FIG. 11B is the result of fluorescence intensity to evaluate the effect of interferon-α by a fluorescence reader. The data was taken from two independent experiments and each was the average readings from 3 wells. The result indicates that interferon-α decreased the damage from thioacetamide in Huh-7$_{PALB-EGFP}$ and immortalized HSC coculture. The fluorescence was expressed by Huh-7$_{PALB-EGFP}$.

One day later, 1000, 5000, 10000 IU/ml of interferon-α(F. Hoffman-La Roche, Ltd.) was added into cells respectively. Three hours later, 100 mM of thioacetamide (Sigma-Aldrich, Co.) was added to damage the cells. After 24 hours, methylene blue assay was conducted for analyzing the cell activity. The result is shown in FIG. 11A. In the meantime, the intensity of green fluorescence was determined by a fluorescence reader, and the result is shown in FIG. 11B. Both experimental results corresponded to each other and further confirmed that interferon-αdecreased cell damaged by thioacetamide in the present cell model for drug screening.

Figure 11C:
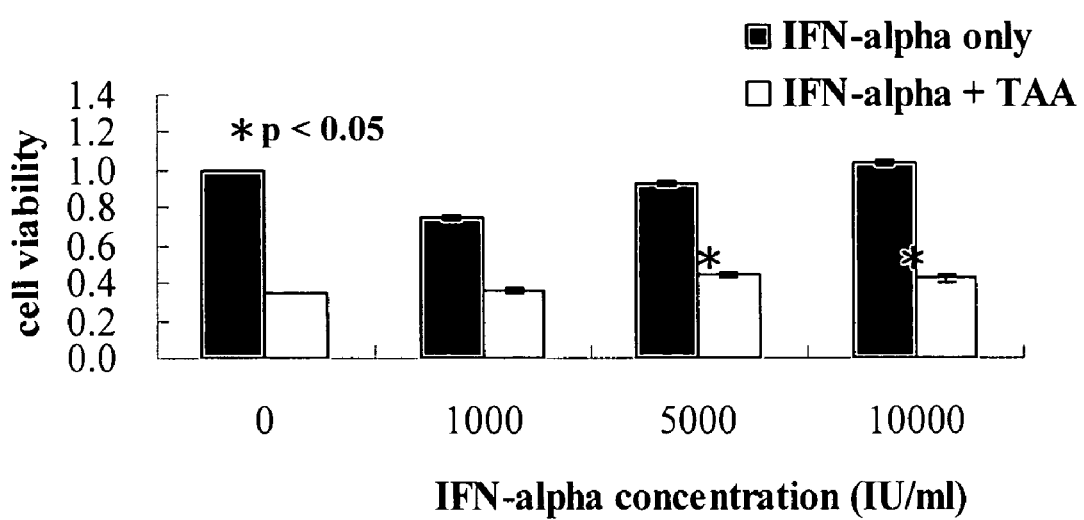
FIG. 11C is the result of methylene blue assay to evaluate the effect of interferon-α. The result indicates that interferon-α decreased the damage from thioacetamide in immortalized hepatocyte THLE-2 and immortalized HSC coculture.

To compare the cells in the present example with the normal hepatocytes and HSCs after drug treatment, immortalized human hepatocytes THLE-2 (ATCC NO: CRL-2706, normal primary hepatocytes immortalized by SV40 large T antigen gene) and untransfected human HSCs were co-cultured following procedures described as the above. After 24 hours, 1000,5000,10000 IU/ml of interferon-αwere added. Thioacetamide was applied to damage the cells after 3 hours. After another 24 hours, the cell activity was examined by methylene blue assay, and the result is shown as FIG. 11C. The result corresponds to that of the cell model for drug screening with pLpLhyg-P$_{Alb5/3}$-EGFP transfected cells (FIG. 11A).

Although the present invention has been explained in relation to its preferred embodiment, it is to be understood that many other possible modifications and variations can be made without departing from the scope of the invention as hereinafter claimed.

What is claimed is:

1. A cell culturing model comprising co-cultured human hepatocytes and human hepatic stellate cells (HSCs) having a cell specific regulatory sequence operatively linked to a heterologous reporter gene nucleotide sequence, and wherein said cell specific regulatory sequence is a human hepatic stellate cell specific promoter comprising a collagen type 1 promoter having the nucleotide sequences selected from the group consisting of SEQ ID NO. 14 and SEQ ID NO. 15.

2. The cell culturing model of claim 1, wherein said human hepatocytes and human HSCs are co-cultured with a culture medium and a culture material which is coated with an extracellular matrix.

3. The cell culturing model of claim 2, wherein said extracellular matrix is collagen or Matrigel.

4. The cell culturing model of claim 1, wherein a ratio of initial concentration of said human hepatocytes and human HSCs is 1:10.

5. The cell culturing model of claim 1, wherein said co-cultured human hepatocytes and human HSCs are mixed co-cultured or separated co-cultured.

6. The cell culturing model of claim 1, wherein the nucleotide sequence is SEQ ID NO. 14.

7. The cell culturing model of claim 1, wherein the nucleotide sequence is SEQ ID NO. 15.

8. The cell culturing model of claim 1, wherein said reporter gene encodes β-galactosidase, luciferase or a fluorescence protein.

9. The cell culturing model of claim 1, wherein said reporter gene encodes a fluorescence protein.

10. The cell culturing model of claim 9, wherein said fluorescence protein is enhanced green fluorescence protein (EGFP).

11. The cell culturing model of claim 9, wherein said fluorescence protein is Discosoma sp. red fluorescent protein (DsRed).

12. The cell culturing model of claim 1, wherein the cells having a cell specific regulatory sequence operatively linked to a heterologous reporter gene nucleotide sequence further comprise a nucleotide sequence fragment of an antibiotic resistance gene.

13. The cell culturing model of claim 12, wherein said antibiotic resistance gene is a hygromycin resistance gene or neomycin resistance gene.

14. The cell culturing model of claim 1, wherein said cell specific regulatory sequence and said reporter gene are delivered into said cells by a liposome-mediated method.

15. The cell culturing model of claim 1, wherein the cells having a cell specific regulatory sequence operatively linked to a heterologous reporter gene nucleotide sequence further comprise a nucleotide sequence of immortalization gene to immortalize the cells.

16. The cell culturing model of claim 15, wherein said immortalization gene is Human telomerase reverse transcriptase catalytic subunit (hTERT).

17. The cell culturing model of claim 15, wherein said nucleotide sequence of immortalization gene is delivered to said cells by a liposome-mediated method.

18. A cell culturing model comprising co-cultured human hepatocytes and human hepatic stellate cells (HSCS) a cell specific regulatory sequence and a nucleotide sequence fragment of a reporter gene, wherein the cell specific regulatory sequence is a hepatocyte specific promoter or a hepatic stellate cell specific promoter having a sequence selected from the group consisting of SEQ ID NO: 14 and SEQ ID NO: 15 and the nucleotide fragment of the reporter gene is a nucleotide sequence that encodes for a product selected from the group consisting of β-galactosidase, chloramphenicol acetyl transferase (CAT), luciferase and a fluorescence protein.

19. The cell culturing model according to claim 18, wherein the nucleotide sequence of said promoter is SEQ ID NO. 14.

20. The cell culturing model according to claim 18, wherein the nucleotide sequence of said promoter is SEQ ID NO. 15.

* * * * *